United States Patent [19]
Furuya et al.

[11] 4,014,928
[45] Mar. 29, 1977

[54] PROCESS FOR PURIFYING α-AMINO ACIDS

[75] Inventors: Osamu Furuya; Koichi Wada, both of Tokyo; Yoshihiko Hosaki, Yokohama; Nobutake Mihara, Kawasaki, all of Japan

[73] Assignee: Showa Denko Kabushiki Kaisha, Tokyo, Japan

[22] Filed: July 31, 1975

[21] Appl. No.: 600,859

[30] Foreign Application Priority Data

Aug. 8, 1974 Japan .............................. 49-90231

[52] U.S. Cl. .................... 260/534 R; 260/534 C
[51] Int. Cl.² ............................................ C07C 99/12
[58] Field of Search ..................... 260/534 C, 534 R

[56] References Cited

UNITED STATES PATENTS

| | | | |
|---|---|---|---|
| 2,335,997 | 12/1943 | Carlson et al. | 260/534 C |
| 2,819,303 | 1/1958 | Griffith et al. | 260/534 C |
| 3,875,221 | 4/1975 | Mihara et al. | 260/534 C |
| 3,935,256 | 1/1976 | Verbeeck | 260/534 C |

Primary Examiner—Joseph E. Evans
Attorney, Agent, or Firm—Fitzpatrick, Cella, Harper & Scinto

[57] ABSTRACT

A process for purifying an α-amino acid containing cyano impurities comprising heating an aqueous solution of the α-amino acid in the form of its alkali metal salt in the presence of an alkali metal hydroxide to decompose the cyano impurities.

8 Claims, No Drawings

PROCESS FOR PURIFYING α-AMINO ACIDS

This invention relates to a process for purifying α-amino acids containing cyano ingredients as impurities.

In most cases, synthesized α-amino acids contain small amounts of cyano ingredients. One known method to synthesize α-amino acids, especially lower α-amino acids, comprises preparing a cyanohydrin from hydrocyanic acid and an aldehyde, aminating the cyanohydrin with ammonia to form an -60 -aminonitrile, converting it to an alkali metal salt of α-amino acid by alkaline hydrolysis, and finally neutralizing the salt with an acid to form an α-amino acid. Similar methods have also been known in which instead of the first and second steps above, hydrocyanic acid, aldehyde and ammonia are reacted simultaneously ("Strecker method"), or ammonium carbonate is used instead of ammonia to allow the process to go through the resulting hydantoin. In any of these methods, the final products unavoidably contain small amounts of hydrocyanic acid or cyanohydrin used as the starting material or by-products which become cyanogen compounds upon decomposition. These impurities containing a cyano group or capable of yielding a CN ion upon decomposition will be referred to hereinbelow as cyano ingredients or cyano impurities.

Since α-amino acids are frequently used as food or feed additives, they are not permitted to contain toxic amounts of cyano impurities, and it is necessary to remove the impurities completely or to tiny amounts below the allowable limit.

Cyano impurities will be described below with particular reference to the synthesis of D,L-alanine. An aqueous solution of α-aminopropionitrile is prepared by reacting an aqueous solution of acetaldehyde with hydrocyanic acid to form lactonitrile, and by reacting it with a large excess of ammonia. Hydrolysis of the product with sodium hydroxide affords an aqueous solution of sodium α-aminopropionate (D, L-alanine, sodium salt). This aqueous solution contains a small amount of cyano impurities in addition to the by-product sodium iminodipropionate. The cyano impurities are present mainly in the form of sodium cyanide. The sodium cyanide is considered to be derived not only from the unreacted portion of the starting hydrocyanic acid but also from cyano groups dissociated during the hydrolysis of the intermediate lactonitrile. Thus, even when lactonitrile substantially free from hydrocyanic acid is used as a starting material, the resulting aqueous solution of a sodium salt of D,L-alanine contains a small amount of sodium cyanide. In addition to sodium cyanide, the product also contains traces of cyano ingredients of unknown chemical composition which are detected by analysis as CN.

One method for separating D, L-alanine from an aqueous solution of sodium α-aminopropionate comprises subjecting the aqueous solution to a cation exchange treatment to remove the Na ion, concentrating and/or cooling the residue, and separating the resulting crystals of D, L-alanine. At this time, the mother liquor containing cyano impurities adheres to the surface of the alanine crystals collected or is occluded within the crystals. Hence, the inclusion of traces of cyano impurities in the final product cannot be avoided. Another separating method involves neutralizing an aqueous solution of sodium α-aminopropionate with sulfuric acid, and fractionally crystallizing the resulting aqueous solution containing alanine and sodium sulfate to obtain first sodium sulfate and then alanine. In this method, too, the cyano impurities in the mother liquor inevitably come into the final product at the time of separating the crystals. It is apparent therefore that whatever other methods of separation may be used, an attempt to separate solid alanine from a solution containing cyano impurities will end in the same result.

While our description has been directed to the synthesis of alanine, it is obvious that cyano impurities will be likewise included in the final product in the synthesis of glycine from formaldehyde and hydrocyanic acid or from the corresponding cyanohydrin, and in the synthesis of other α-amino acids.

In order to provide α-amino acids free from cyano impurities, it is necessary either to remove the cyano impurities from synthesized α-amino acid products, or to decompose the cyano impurities during the synthesizing process. It is an object of this invention to provide a process of purifying α-amino acids which can be performed with commercial advantage. The process of this invention can be applied also to synthesized α-amino acid products which contain cyano impurities, but is especially advantageous in that it can be applied during their synthesis.

In the field of waste water treatment, it is the general practice to decompose or remove small amounts of cyano impurities contained in waste waters by, for example, a method of oxidative decomposition using an oxidizing agent such as hydrogen peroxide or sodium hyprochlorite, an oxidation-combustion method, a hydrolysis method using ammonia, electrical methods using silent discharge or electrolysis, or a decomposition method using microorganisms. It is known that hydrocyanic acid decomposes when heated to a high temperature in an alkaline or acidic aqueous solution, and waste water treating methods utilizing this fact have been performed industrially in plating plants.

However, a method for decomposing cyano impurites in a system containing useful α-amino acids has not been known heretofore. The process of this invention basically relates to a method of decomposing cyano impurities in the presence of an alkali hydroxide. Such a process has been considered as infeasible in view of the conventional technical knowledge, because α-amino acids are generally weak to heat and degenerate or decompose at high temperatures at which the cyano impurities can be decomposed with alkali hydroxides. As a matter of fact, α-amino acids become degenerated and colored at substantially lower temperatures than the decomposition temperatures described in the literature, and thus lose their value as commercial products. For example, it is described in the literature that D,L-alanine decomposes at 264° C. Actually, however, when it is heated at a temperature of 80° to 100° C. for 1 to 2 hours or longer, it degenerates and turns brown. The decomposition temperature of glycine is known to be 233° C., but in fact, it becomes degenerated and colored at about 100° C. The same can be said with regard to other α-amino acids. On the other hand, the temperature at which cyano impurities are effectively decomposed with an aqueous solution of an alkali hydroxide is 100° C. or higher.

Since α-amino acids are weak to heat, it was not expected that cyano impurites would be able to be decomposed under heat with alkali hydroxides in an aqueous system in which the α-amino acids are present. Suprisingly, however, it has now been found that in the form of alkali metal salts, α-amino acids become very stable to heat in aqueous systems, and can, without degeneration or coloration, withstand high temperatures sufficient to decompose cyano impurities present in the system with alkali hydroxide. It was confirmed that for example, D, L-alanine and glycine, both in the form of alkali metal salts, are neither colored nor degenerated even when heated in aqueous solution at about 150° to 160° C. for several hours. Thus, α-amino acids, in the form of alkali metal salts, become extremely stable to heat in aqueous solution, and this heat stability does not change even when the alkali hydroxides are present in excess in the aqueous solution. On the other hand, when the aqueous solution contains cyano impurities, these cyano impurities can be easily decomposed by heating in the presence of the excessive alkali hydroxides. This finding has led to the accomplishment of this invention.

According to this invention, therefore, a process for purifying an α-amino acid containing cyano impurities is provided which comprises heating an aqueous solution of the α-amino acid in the form of its alkali metal salt in the presence of an alkali metal hydroxide to decompose the cyano impurities present in the aqueous solution, the heating temperature being one sufficient to decompose the cyano impurities without involving the decomposition of the α-amino acid in the form of its alkali metal salt.

Some preferred embodiments of the present invention will be described below.

The process of this invention can be performed using α-amino acid products containing cyano impurities as starting materials, and is also applicable during the synthesis of the α-amino acids. As previously stated, the synthesis of α-amino acids involves a step of forming alkali metal salts of the α-amino acids. Accordingly, it is more rational and economical to apply the process of this invention to this step.

The process of this invention can be applied to any α-amino acid containing cyano impurities. But it is applicable especially preferably to lower α-amino acids such as alanine or glycine. The alkali metal in the alkali metal salt of α-amino acid and the alkali metal hydroxide to decompose the cyano impurities may be any alkali metal, but the use of sodium is usually most preferred and economical. The concentration of the alkali metal salt of α-amino acid in aqueous solution is not particularly restricted.

The amount of the alkali metal hydroxide is one sufficient to maintain the pH of the aqueous solution at at least 13.5. The amount of the alkali metal hydroxide to be consumed increases with increasing amount of cyano impurities present in the aqueous solution. Hence, according to the amount of the cyano impurities present, the alkali metal hydroxide must be added in an amount which is sufficient to maintain the pH of the aqueous solution at at least 13.5 even after the heat-decomposition procedure. The upper limit of the amount of the alkali metal hydroxide to be added is not restricted, but an excessive amount is not desirable because it must be neutralized after the decomposition procedure. Aqueous solutions of alkali metal salts of α-amino acids are somewhat alkaline. For example, a 25% aqueous solution of a sodium salt of D, L-alanine has a pH of about 12.4. However, even when such an alkaline aqueous solution is heated without adding an alkali metal hydroxide, the cyano impurities present there are not decomposed.

The degree of decomposition of cyano impurities is higher with higher heat-treating temperatures, and the treatment time can be shortened. Accordingly, temperatures of 100° C. or more at which the cyano impurities are effectively decomposed are employed in this invention. However, excessively high temperatures are very likely to cause degeneration of alkali salts of α-amino acids as important ingredients. The upper limit of the temperature range should therefore be specified as 180° C. The especially preferred temperatures range is 130° to 160° C. The pressure is an autogeneous pressure corresponding to the temperature applied. In the industrial performance of the process of his invention, it is convenient to use a pressure vessel and introduce superheated steam into the aqueous solution.

The heating time depends upon the temperature applied and the desired degree of decomposition of cyano impurities, but usually, a satisfactory decomposition of cyano impurities can be achieved by performing the heating for 0.5 to 5 hours. After the decomposition procedure, an acid is added to the aqueous solution to neutralize it in a customary manner. This results in the conversion of the alkali metal salt of α-amino acid to a free acid. On cooling and/or concentration, the desired α-amino acid completely or substantially free from cyano impurities can be separated.

The following Examples specifically illustrate the present invention.

EXAMPLE 1

An 80% aqueous solution of commercially available lactonitrile was diluted with water to a concentration of 50%, and 6 moles, per mol of the lactonitrile, of liquid ammonia was added. They were reacted in an autoclave to form an aqueous solution of α-aminopropionitrile. At atmospheric pressure, the ammonia was flushed away, and then, the α-aminopropionitrile was reacted under heat with a 20% aqueous solution of sodium hydroxide in an amount of 1.2 moles per mole of the α-aminopropionitrile to afford an aqueous solution of sodium α-aminopropionate.

As one example, the chemical composition of the resulting product was as follows:

| | |
|---|---|
| Sodium α-aminopropionate | 25.2% by weight |
| Sodium iminodipropionate | 2.9% by weight |
| Sodium hydroxide | 1.9% by weight |
| Cyano impurities (as CN) | 0.8% by weight |
| Water and other ingredients | balance |
| pH | above 14 |
| Coloration(APHA) | 2000 |

300 g of the product was placed in a 500 ml. autoclave, and heated in an oil bath. It was heated with stirring at 150° C. for 3 hours. The pressure was initally 4.5 Kg/cm$^2$.G, and at the end of 3 hours, rose to 5.0 Kg/cm$^2$.G. The reaction solution was cooled and 295 g of a product of the following chemical composition was obtained.

| | |
|---|---|
| Sodium α-aminopropionate | 25.1% by weight |
| Sodium iminodipropionate | 2.9% by weight |
| Sodium hydroxide | 1.7% by weight |
| Cyano impurities (as CN) | 0.01% by weight |
| Water and other ingredients | balance |
| pH | above 14 |

| | |
|---|---|
| Coloration (APHA) | 1200 |

Thus, 97.9% of the sodium α-aminopropionate was recovered, and in view of the handling loss, the degree of decomposition of it was less than 1%. On the other hand, the degree of decomposition of the cyano impurities was 98 to 99%.

The coloration of the reaction solution was reduced considerably by the above treatment. When the treated solution was neutralized with sulfuric acid, slight foaming began at a pH of about 6. The foams were carbon dioxide, and it is presumed that the decomposed cyano impurities changed to sodium carbonate and nitrogen gas.

EXAMPLE 2 (COMPARISON)

Commercially available D, L-alanine was dissolved in water, and a 48% aqueous solution of sodium hydroxide was added in an equivalent weight. The pH of the solution became 12.4. Sodium cyanide was added to prepare a solution of the following composition.

| | |
|---|---|
| Sodium α-aminopropionate | 26.0% by weight |
| Cyano impurities (as CN) | 0.8% by weight |
| Water and other ingredients | balance |
| pH | 12.4 |

When the solution was heated at 150° C. for 3 hours in the same way as in Example 1, the chemical composition of the solution changed as follows:

| | |
|---|---|
| Sodium α-aminopropionate | 25.9% by weight |
| Cyano impurities (as CN) | 0.74% by weight |
| Water and other ingredients | balance |
| pH | 12.4 |

It was thus found that in the absence of an alkali hydroxide, the cyano impurities were scarcely decomposed.

EXAMPLE 3

A 48% aqueous solution of sodium hydroxide was added to the starting solution used in Example 2 until its concentration became 2.0% by weight, thereby to adjust the pH of the solution to above 14. The solution was then heated at 150° C. for 3 hours. The amount of the cyano impurities was decreased to 0.01% by weight. The degree of decomposition of sodium α-aminopropionate was less than 1%.

EXAMPLE 4

To a 50% aqueous solution of commercially available glycolonitrile was added liquid ammonia in an amount of 6.0 moles per mole of the glycolonitrile. The solution was then reacted in an autoclave to form an aqueous solution of glycinonitrile. The pressure was returned to atmospheric pressure, and the ammonia was removed by flushing. The residual solution was carefully distilled at reduced pressure to form glycinonitrile having a purity of about 94%. The amount of cyano impurities (as CN) was 0.4%.

The resulting glycinonitrile was diluted with water to form a 50% aqueous solution of glycinonitrile, and a 48% aqueous solution of sodium hydroxide was added in an amount of 1.1 moles per mole of the glycinonitrile to hydrolyze the glycinonitrile and thus, to form an aqueous solution of sodium amino-acetate having the following chemical composition.

| | |
|---|---|
| Sodium aminoacetate | 51.4% by weight |
| Iminodiacetic acid | 1.0 by weight |
| Sodium hydroxide | 2.2% by weight |
| Cyano impurities (as CN) | 0.1% by weight |
| Water and other ingredients | 45.3% by weight |
| pH | above 14 |

The resulting aqueous solution was heated in an autoclave 150° C. for 3 hours in the same way as in Example 1. The degree of decomposition of the sodium aminoacetate was 0.8%, and the degree of decomposition of the cyano impuritieis was 97.2%.

EXAMPLE 5

Using the starting solution used in Example 4, the same procedure as in Example 1 was repeated except that the reaction temperature and time was varied. The degrees of the decomposition of sodium aminoacetate and cyano impurities changed as tabulated below.

| Reaction time (hours) | Reaction temperature (° C) | Degree of decomposition (%) | |
|---|---|---|---|
| | | Sodium amino-acetate | Cyano impurities |
| 1 | 150 | 0.0 | 78.0 |
| 2 | 150 | 0.2 | 87.3 |
| 1 | 120 | 0.0 | 64.0 |
| 2 | 120 | 0.0 | 79.0 |
| 3 | 120 | 0.0 | 90.0 |

What we claim is:

1. A process for purifying a synthesized α-amino acid containing cyano impurities which comprises heating an aqueous solution of the α-amino acid in the form of its alkali metal salt in the presence of an alkali metal hydroxide to decompose the cyano impurities present in the aqueous solution without decomposing the alkali metal salt of the α-amino acid, wherein the heating temperature is 130° to 160° C., wherein alkali metal hydroxide is present in said aqueous solution in an amount sufficient to maintain a pH in said aqueous solution of at least 13.5, and wherein said synthesized α-amino acid is produced by aminating a cyanohydrin with ammonia to form the corresponding α-aminonitrile, converting the α-aminonitrile to an alkali metal salt of the corresponding α-amino acid by alkaline hydrolysis and finally neutralizing the salt with an acid to form the corresponding free α-amino acid.

2. The process of claim 1 wherein said α-amino acid is D,L-alanine or glycine.

3. The process of claim 2 wherein the heating is conducted for a period of time of from 0.5 to 5 hours.

4. The process of claim 2 wherein said alkali metal hydroxide is sodium hydroxide and wherein the alkali metal of the alkali metal salt of the α-amino acid is sodium.

5. The process of claim 2 wherein said heating is conducted in a pressure vessel and superheated steam is introduced into said aqueous solution during said heating step.

6. The process of claim 2 which further includes the steps of neutralizing said aqueous solution after the decomposition of said cyano impurities, said recovering said α-amino acid.

7. The process of claim 2 wherein said cyanohydrin is glycolonitrile, and wherein said α-aminonitrile is glycinonitrile.

8. The process of claim 2 wherein said cyanohydrin is lactonitrile, and wherein said α-aminonitrile is α-aminopropionitrile.

* * * * *

UNITED STATES PATENT AND TRADEMARK OFFICE
CERTIFICATE OF CORRECTION

PATENT NO. : 4,014,928
DATED : March 29, 1977
INVENTOR(S) : OSAMU FURUYA, ET AL

It is certified that error appears in the above-identified patent and that said Letters Patent are hereby corrected as shown below:

Column 1, line 11, "60" should read --$\alpha$--.

Signed and Sealed this fifth Day of July 1977

[SEAL]

Attest:

RUTH C. MASON
*Attesting Officer*

C. MARSHALL DANN
*Commissioner of Patents and Trademarks*